(12) United States Patent
Bakulin

(10) Patent No.: US 8,635,907 B2
(45) Date of Patent: Jan. 28, 2014

(54) REAL-TIME COMPLETION MONITORING WITH ACOUSTIC WAVES

(75) Inventor: Andrey Victorovich Bakulin, Dhahran (SA)

(73) Assignee: Shell Oil Company, Houston, TX (US)

( * ) Notice: Subject to any disclaimer, the term of this patent is extended or adjusted under 35 U.S.C. 154(b) by 643 days.

(21) Appl. No.: 12/744,957

(22) PCT Filed: Nov. 26, 2008

(86) PCT No.: PCT/US2008/084882
§ 371 (c)(1),
(2), (4) Date: Oct. 25, 2010

(87) PCT Pub. No.: WO2009/073520
PCT Pub. Date: Jun. 11, 2009

(65) Prior Publication Data
US 2011/0030467 A1 Feb. 10, 2011

Related U.S. Application Data

(60) Provisional application No. 61/004,877, filed on Nov. 30, 2007, provisional application No. 61/058,944, filed on Jun. 5, 2008.

(51) Int. Cl.
*E21B 49/08* (2006.01)
*E21B 43/00* (2006.01)
*E21B 47/00* (2012.01)
*G01N 15/08* (2006.01)
*G01N 29/07* (2006.01)
*G01N 29/11* (2006.01)

(52) U.S. Cl.
CPC .............. *E21B 49/087* (2013.01); *E21B 47/00* (2013.01); *E21B 43/00* (2013.01); *G01N 15/08* (2013.01); *G01N 29/07* (2013.01); *G01N 29/11* (2013.01); *G01N 2015/084* (2013.01)
USPC ................. 73/152.05; 73/152.16; 73/152.31; 73/152.32; 73/152.36; 73/152.55; 73/152.58; 73/597; 73/599; 166/250.01; 166/369; 702/6

(58) Field of Classification Search
CPC ......... E21B 43/00; E21B 43/12; E21B 47/00; E21B 47/10; E21B 47/101; E21B 49/08; E21B 49/087; E21B 2043/00; E21B 2043/12; G01N 15/08; G01N 29/07; G01N 29/11; G01N 2015/08; G01N 2015/084
USPC ............... 73/152.05, 152.16, 152.31–152.32, 73/152.36, 152.41, 152.55, 152.58, 597, 73/599; 166/250.01, 269; 367/30–31; 702/6, 13, FOR. 102
See application file for complete search history.

(56) References Cited

U.S. PATENT DOCUMENTS 3,390,377 A * 6/1968 Grine et al. ..................... 367/75
4,888,740 A * 12/1989 Brie et al. ....................... 367/30

(Continued)

FOREIGN PATENT DOCUMENTS

CN 1402811 A 3/2003 ............. E21B 47/10
GB 2401385 11/2004 ............. E21B 43/08

(Continued)

OTHER PUBLICATIONS

Medlin, W.L., et al: Fracture Diagnostics with Tube Wave Reflection Logs, Jrnl. of Petroleum Technology, pp. 239-248.

*Primary Examiner* — Thomas P Noland

(57) ABSTRACT

A method for monitoring fluid flow through a downhole device, comprises a) providing an acoustic tube wave in fluid in the device; b) measuring the acoustic tube wave after it has passed through the fluid in the device; and c) assessing the permeability of the device by measuring the attenuation of the acoustic signal. Changes in velocity of the acoustic signal may also be measured. The device may be a permeable downhole device such as a sand screen the measurements in step b) are made using a plurality of sensors deployed in the hole. The method may further including the step of cross-correlating a signal received at a first receiver with signals received at additional sensors so as to obtain an effective response as if the signal had been emitted from a source at the position of said first receiver.

15 Claims, 2 Drawing Sheets

(56) References Cited

U.S. PATENT DOCUMENTS

| | | | |
|---|---|---|---|
| 5,331,604 A * | 7/1994 | Chang et al. | 367/31 |
| 5,784,333 A * | 7/1998 | Tang et al. | 367/30 |
| 6,327,538 B1 | 12/2001 | Chin | 702/18 |
| 6,513,591 B1 * | 2/2003 | Heijnen | E21B 47/101 |
| 6,747,915 B2 | 6/2004 | Calvert | 367/46 |
| 6,854,327 B2 | 2/2005 | Rambow et al. | 73/250 |
| 7,894,300 B2 * | 2/2011 | Hawthorn et al. | 73/152.18 X |
| 2003/0125878 A1 | 7/2003 | Bakulin et al. | 702/14 |
| 2004/0246816 A1 | 12/2004 | Ogle | 367/35 |
| 2006/0034152 A1 | 2/2006 | Korneev | 367/31 |
| 2006/0235617 A1 | 10/2006 | Sinha et al. | 702/6 |
| 2007/0195643 A1 | 8/2007 | Bakulin et al. | 367/38 |
| 2009/0145600 A1 * | 6/2009 | Wu et al. | 166/250.02 |

FOREIGN PATENT DOCUMENTS

| | | | | |
|---|---|---|---|---|
| WO | WO 2007001746 A1 * | 1/2007 | | G01V 1/50 |
| WO | WO2008064100 | 5/2008 | | G01V 1/36 |

\* cited by examiner

REAL-TIME COMPLETION MONITORING WITH ACOUSTIC WAVES

CROSS REFERENCE TO RELATED APPLICATIONS

The present application claims priority to International Application PCT/US2008/084882, filed on 26 Nov. 2008, which claims priority to U.S. application Ser. No. 61/004,877, filed on Nov. 30, 2007, and Ser. No. 61/058,944, filed on Jun. 5, 2008, each of which is incorporated herein in its entirety

STATEMENT REGARDING FEDERALLY SPONSORED RESEARCH OR DEVELOPMENT

Not applicable.

FIELD OF THE INVENTION

The inventions disclosed and taught herein relate generally to the field of subterranean well monitoring, and more specifically to methods and systems for the real-time acoustic monitoring of completed wells and the surrounding subterranean regions.

BACKGROUND OF THE INVENTION

Completions lie at the heart of deepwater production and constitute a large portion of the overall well cost. Great multidisciplinary effort is invested in designing them. This contrasts greatly with the production stage, where little information is available to detect problems, optimize the inflow and prevent expensive work-overs. Sand screen plugging, incomplete packing, development of "hot spots" in screens, destabilization of the annular pack, fines migration, near-wellbore damage, cross-flow, differential depletion, compartmentalization, compaction represent a typical list of challenges that are extremely difficult to decipher based on just several permanent pressure and temperature gauges. Many problems can be identified by production logging, but it is costly and not in real time. Permanent pressure and temperature sensors placed across the sandface can provide critical information for diagnosing the completion problems and the service industry is developing tools to make such sensing feasible in the future. However these new pressure and temperature data are unlikely to lead to unambiguous identification of the problems above because of multitude of parameters characterizing complex completions and reservoirs that remain unconstrained by our data.

For example, there is an issue of underperforming hydrocarbon production wells in the Gulf of Mexico. "Well performance" absorbs large-scale reservoir issues such as compartmentalization as well as changes in local well skin with time that further comprises of completion, perforations and near-wellbore effects. Therefore, multiple explanations can be given to the problem. Apparent compartmentalization and ubiquitous U-shaped boundaries can be one answer on a "reservoir" scale. Yet those boundaries are rarely confirmed by 4D seismic or other data. Shale draping is an alternative reservoir-scale scenario that can lead to well underperformance. Another wellbore-scale explanation suggests that well productivity declines with time due to loss of so called "kh" product where k and h are reservoir permeability and thickness correspondingly. The differential depletion model argues that this loss occurs mainly due to reduction in producing thickness although the exact mechanisms of flow impairment are still debated. Similarly, reduction in permeability is another alternative explanation, although the amount of this reduction (85-90%) is not consistent with laboratory measurements. Existing sparse data from wells can support any of these scenarios, confirming that the problem is under-constrained. In order to distinguish between these quite different scenarios, there is a need for more downhole data at various scales that can unambiguously characterize various components of the production system.

In the context of deepwater completions there is an additional emphasis on sand control because it is believed that managing produced sand is generally a costly and mostly unworkable solution for the Gulf of Mexico, although it may work well in other places where there is some grain-to-grain cementation present. The presence of sand control media between the reservoir and the wellbore introduces additional cost, complexity and requires proper management. The goal is a solution that is robust enough to control sand production for the life of the reservoir, avoiding impairment and the need for any intervention. To come up with a sand control system that is less prone to problems, the root cause of existing problems must first be understood. Once issues are fully understood, smart, on-demand intervention or remediation may become possible. The high cost of deepwater well devices (sand screens etc) and intervention can justify the presence of smart surveillance tools that would not be economical in other environments. In addition, the surveillance tools preferably need to last for the life of the reserve.

SUMMARY OF THE INVENTION

The present invention provides a system and method for monitoring downhole permeable devices such as sand screens. According to some embodiments, a method for monitoring fluid flow through a downhole device, comprises a) providing an acoustic tube wave in fluid in the device; b) measuring the acoustic tube wave after it has passed through the fluid in the device; and c) assessing the permeability of the device by measuring the attenuation of the acoustic signal. Changes in velocity of the acoustic signal may also be measured.

The device may be is a permeable downhole device and step c) may further include determining that the device is at least partially plugged by detecting at least one of a reduction in attenuation or a reduction in velocity loss in the tube wave as it passes through the device.

The device may be a sand screen; the measurements in step b) may be made using a plurality of sensors deployed in the hole; and the sensors may be fiber optic sensors. The method may further including a step of cross-correlation a signal received at a first receiver with signals received at additional sensors so as to obtain an effective response as if the signal had been emitted from a source at the position of the first receiver.

Step c) may further include determining that the device is not plugged by detecting that a fast tube wave passing through the device is slowed at low frequencies but is accelerated at high frequencies; determining that the device is not plugged by measuring a fast wave and detecting a relatively strong attenuation of said fast wave in a frequency range of 350-700 Hz; or determining that the device is not plugged by detecting a slow tube wave that has been transformed into a complex packet with reduced amplitude and velocity. The method may further include the step of determining the relative permeability of the device by detecting a frequency band having a relatively high degree of attenuation and comparing the frequency of the band to that of a frequency band having a relatively high degree of attenuation in a different measurement.

In other embodiments, the invention provides a method for producing hydrocarbons from a hydrocarbon-bearing formation, comprising producing hydrocarbons through a permeable downhole device and monitoring the flow through the device using the methods described herein. The present invention includes a system for real-time monitoring of completions by providing the ability to assess changes in permeability occurring in the sand screen and gravel pack devices, as well as individual perforations using acoustic waves. It is complementary to other in-well monitoring methods, such as that disclosed in U.S. Pat. No. 6,854,327, that allow monitoring structural integrity (static deformations) of sand screens and thus understanding compaction and other strain-related conditions.

The present acoustic monitoring method can serve as a permanently installed monitor of the quality of the sandface. The acoustic monitoring methods constantly conduct both active checks of the sandscreen and its environment and passive monitoring of the reservoir. Early detection and proper diagnostics follow as a natural outcome of permanent monitoring, so that proper treatment (work-over) can be delivered before issues get out of hand. Permanent monitoring can also serve as an additional insurance to safeguard expensive completion and sand control devices, as well as the borehole itself. In addition, methods such as described herein can deliver streams of new data to that can enhance understanding of other sand-screen and completion issues and eventually contribute to proper resolution of many "well underperformance" problems.

The inventions disclosed and taught herein are directed to methods and applications of real-time acoustic monitoring of completions and gravel packs. In accordance with a first embodiment of the present disclosure, a method for enhancing the recovery of hydrocarbons from a hydrocarbon bearing formation employing recovery fluids is described, wherein the method comprises real-time acoustic monitoring of the stability and/or permeability of the completion. Further embodiments of the present invention include methods for producing hydrocarbons from a hydrocarbon-bearing formation while monitoring the stability of a sand-screened completion are described, wherein the method comprises real-time acoustic monitoring of the completion using an acoustic model during the production process.

In yet another embodiment of the present disclosure, methods for maintaining the stability or permeability changes of a wellbore during drilling or well servicing operations, or during production or enhanced recovery operations, or during sand-screened completions. The present methods may include using fluids introduced into the wellbore to facilitate the operations are described. Still other embodiments of the present methods ma comprise generating a real-time acoustic monitoring model; monitoring the wellbore using acoustic tube waves to monitor changes in the wellbore; continuing to update the model and continuing to adjust on a real-time basis the properties of the fluids as needed to maintain or enhance the production permeability during the operation.

BRIEF DESCRIPTION OF THE SEVERAL VIEWS OF THE DRAWINGS

The following figures form part of the present specification and are included to further demonstrate certain aspects of the present invention. The invention may be better understood by reference to one or more of these figures in combination with the detailed description of specific embodiments presented herein.

Figure 1:
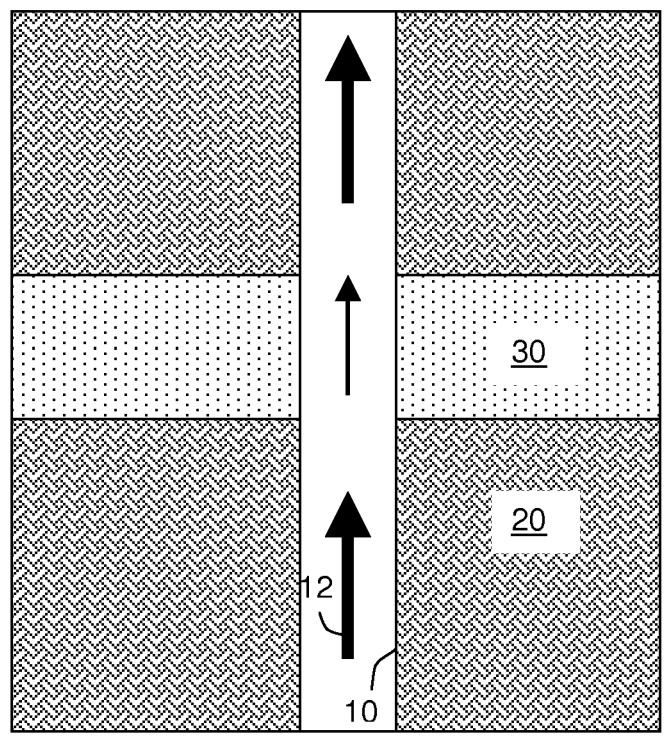
FIG. 1 schematically illustrates the effect of permeability on acoustic waves using a model of a reservoir.

While the inventions disclosed herein are susceptible to various modifications and alternative forms, only a few specific embodiments have been shown by way of example in the drawings and are described in detail below. The figures and detailed descriptions of these specific embodiments are not intended to limit the breadth or scope of the inventive concepts or the appended claims in any manner. Rather, the figures and detailed written descriptions are provided to illustrate the inventive concepts to a person of ordinary skill in the art and to enable such person to make and use the inventive concepts.

DETAILED DESCRIPTION

It will be understood that the use herein of a singular term, such as, but not limited to, "a," is not intended as limiting of the number of items. Also, the use of relational terms, such as, but not limited to, "top," "bottom," "left," "right," "upper," "lower," "down," "up," "side," and the like are used in the written description for clarity in specific reference to the Figures and are not intended to limit the scope of the invention or the appended claims. Additionally, in this description, the terms "up" and "down"; "upward" and "downward"; "upstream" and "downstream"; and other like terms indicating relative positions above or below a given point or element are used in this description to more clearly described some embodiments of the invention. However, when applied to apparatus and methods for use in wells that are deviated or horizontal, such terms may refer to a left to right, right to left, or other relationship as appropriate. Discussion of singular elements can include plural elements and vice-versa.

One aspect of the present invention is the use of a sensor, such as an acoustic sensor, in a well to monitor an operation performed in the well or to monitor various aspects of a downhole tool, system, or device. Other aspects of the invention include the routing of control lines and sensor placement in a sand control completion. By way of example, the present invention may be used in a wellbore that has penetrated a subterranean zone that includes a productive formation. The wellbore may include a casing that has been cemented in place. The casing may have a plurality of perforations that allow fluid communication between the inside of the wellbore and the productive formation. As is known in the art, well tools, such as a sand control completion devices, may be positioned within the casing adjacent to the productive formation, which is to be gravel packed.

As used herein, the term "screen" refers to wire wrapped screens, mechanical type screens and other filtering mechanisms typically employed with sand screens. Screens generally have a perforated base pipe with a filter media (e.g., wire wrapping, mesh material, pre-packs, multiple layers, woven mesh, sintered mesh, foil material, wrap-around slotted sheet, wrap-around perforated sheet, MESHRITE manufactured by Schlumberger, or a combination of any of these media to create a composite filter media and the like) disposed thereon to provide the necessary filtering. The filter media may be made in any known manner (e.g., laser cutting, water jet cutting and many other methods). Sand screens need to have openings small enough to restrict gravel flow, often having gaps in the 60-120 mesh range, but other sizes may be used. The screen element can be referred to as a screen, sand screen, or a gravel pack screen. Many of the common screen types include a spacer that offsets the screen member from a perforated base tubular, or base pipe, that the screen member surrounds. The spacer provides a fluid flow annulus between the screen member and the base tubular. Screens of various types commonly known to those skilled in the art. Note that other types of screens will be discussed in the following description. Also, it is understood that the use of other types of base pipes, e.g. slotted pipe, remains within the scope of the present invention. In addition, some screens have base pipes that are unperforated along their length or a portion thereof to provide for routing of fluid in various manners and for other reasons.

Applicants have created highly effective methods and systems for the real-time acoustic monitoring of sand-screened completions using acoustic waves. These methods and systems can be used to monitor a variety of variables in a completed boreholes, including permeability and changes in permeability across the completed subterranean region.

FIG. 1 is a schematic illustration of an open borehole 10 passing through an impermeable formation 20 in which there is a layer 30 of a porous, permeable material filled with fluid, which is an environment typical for wireline acoustic logging. Within this environment, a tube or Stoneley wave 12 is a fundamental axisymmetric mode that exists from zero frequency. At low frequencies it represents a piston-like motion of the fluid column and dominates wave propagation. When formation shear velocity is larger than the fluid velocity ("fast formation"), as in an impermeable formation, the tube wave is completely trapped—a mode that does not attenuate in impermeable formations. When tube wave encounters a permeable region such as 30, it slows down and attenuates because fluid communication occurs between the formation and the wellbore. This communication leads to an energy loss in the form of leaking slow Biot waves inside the formation. Modeling predicts that at low frequencies, tube-wave velocity will decrease and attenuation will increase with increasing fluid mobility (permeability/viscosity). These predictions have been validated in the laboratory and became a foundation for a "direct" and continuous technique of estimating in-situ permeability from wireline logs. The presence of mudcake restricts fluid communication and makes tube-wave signatures less sensitive to formation permeability. In the limiting case of a hard mudcake, fluid pressures in the borehole and the formation become completely unrelated; tube waves experience no attenuation and slow down and propagate in the same way that they would if the well were surrounded by an impermeable formation.

In addition to the effect of the permeability of the surrounding formation on tube waves, boundaries between formations with different permeabilities also cause reflected tube waves. When the effect of a change in permeability is simulated using a simple model of a permeable reservoir embedded between two impermeable half-spaces, it can been seen that some reflection exists due to mismatch of tube-wave velocities between the layer and the half-spaces. Increases in layer permeability in the simulation lead to dramatic increase in tube-wave reflectivity, especially at low frequencies. The added reflectivity is due to increased fluid communication; a more permeable formation causes a larger reduction in tube-wave velocity inside the layer and therefore larger contrast in properties controlling the reflection. If fluid communication is terminated (e.g. hard mudcake) then all the responses collapse down to the black curve corresponding to impermeable elastic case. This highlights the fact that tube-wave signatures are only affected when fluid communication is present. For a partial fluid communication, responses would fall between elastic impermeable and corresponding open-flow poroelastic solutions.

We have discovered that tube waves are capable of instantly testing the presence or absence of fluid communication across the borehole wall inside a particular layer. If the fluid communication is absent due to present mudcake or lack of formation permeability, then velocity reduction or attenuation is observed. If fluid communication is present, then velocity reduction and attenuation are observed. Similarly, in a reflection configuration, increased fluid communication leads to a larger reflection. In the next sections we illustrate the application of these principles to cased completed boreholes with sand-screened completions.

Cased and Completed Boreholes

Figure 2:
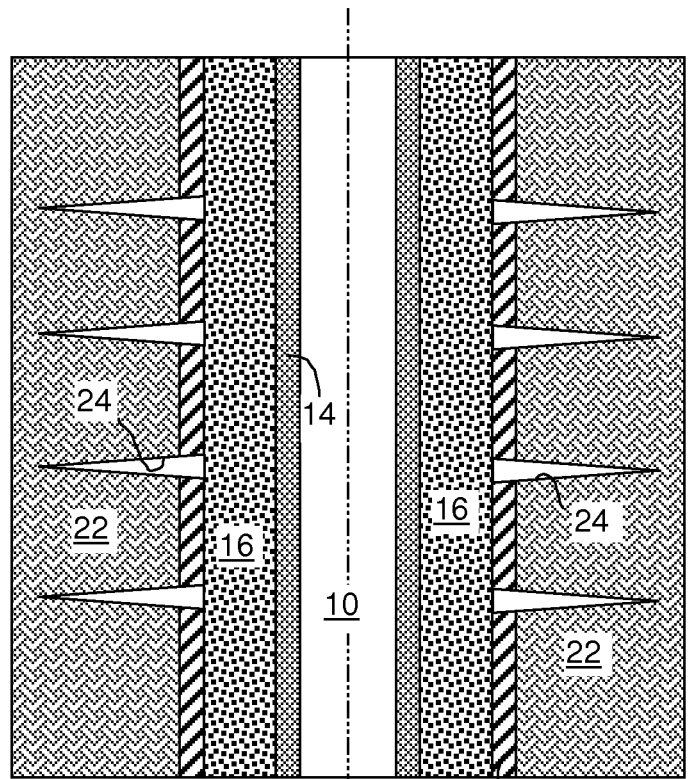
FIG. 2 schematically illustrates a cross-section of a sand-screened completion in a cased borehole.

A cased and completed well has several layers between the formation and the borehole fluid. As shown in FIG. 2, in a simplified model of a sand-screened cased completion the following concentric cylindrical layers are typically present: fluid-filled borehole 10, sand screen 14, gravel sand 16, casing 18, and formation 22. A plurality of perforations 24 in the casing act as communication channels, connecting borehole 10 with formation 22 through casing 18. In open-hole completions, the casing and perforations are absent and formation fluid communicates directly with the borehole through the gravel pack and sand screen. The sand screen and gravel pack prevent migration of reservoir sand into the wellbore as well as maintain the structure of the reservoir around the wellbore.

This more complex model of a completed well has one essential similarity to the simple open-hole model, namely in a flowing well there will be fluid communication across all layers of the completion. Lack of fluid communication in any intermediate layer (screen or perforations) will alter the flow of reservoir fluid into the borehole.

As discussed below, we have discovered that reduced or fluid communication across the sand screen or perforations has a measurable effect on the signatures of tube waves passing through the relevant portion of the borehole. Thus, the present systems and methods can be used to monitor whether permeable downhole devices, including but not limited to sand screens and perforated casings, are allowing the expected level of flow, or are partially or completely plugged. As long as sufficient sensors are in place to provide the necessary resolution, the present systems and methods can be used to locate and quantify the extent of plugging of a permeable downhole device. Still further, we have discovered that the present systems and techniques can be used to monitor dynamic systems in which the rate and pattern of fluid flow is changing, such as a gravel packing process.

There are significant acoustic distinctions between open-hole and sand-screened completions: a) the latter have additional solid layers of sand screen or casing (both made of steel); b) only a single poroelastic layer and a single interface are present in the open-hole model, whereas in the sand-screened completion there are multiple poroelastic layers (perforated casing, formation, gravel sand, sand screen) and multiple poroelastic interfaces between them; c) gravel sand and sand screen are very different from reservoir rocks in that they are very permeable (permeability>100 Darcy); and gravel sand has very low shear velocity (<100 m/s).

The effects of casing and (impermeable) sand screen can be partially understood from studies of wave propagation in producing wells with tubing and casing or open holes with drillpipe. In both cases, the inner pipe and the annulus are filled with the same or a different fluid. A key distinction between these analog models and the sand-screen completion is the following: tubing, drillpipe and casing are completely impermeable, whereas sand screen, gravel sand and casing are highly permeable and, in the normal case, are open to flow; and, the annulus is filled with fluid having no shear rigidity, whereas the gravel sand in the sand-screened completion is likely to have some small shear rigidity.

There are two known techniques that utilize tube waves in producing cased and perforated wellbores for monitoring of hydraulic fracturing. The first technique comprises the use of "tube-wave reflection logs." It analyzes the strength of tube-wave reflections along a perforated interval that was hydraulically fractured. By carrying out tube-wave reflection logging at frequencies ~300-3000 Hz before and after stimulation one can assess the quality of hydraulic fracturing along the perforated interval. The second technique, "hydraulic impedance testing," consists of periodically pulsing a stimulation well with very-low frequency tube waves (<10 Hz) and looking for changes in various signatures of reflected signals to estimate the time of opening and the parameters of a hydraulic fracture behind a perforated casing. In the first technique a source and a receiver are placed in the wellbore next to the fracture and therefore high-frequency reflections can resolve the flow properties of individual vertical intervals of a few meters. In the second technique the signal is sent and received from the wellhead with the result that only very low frequencies can be recorded. As a consequence, this technique has poor vertical resolution and only averaged properties of the whole fracture can be evaluated. Nevertheless, both techniques illustrate the use of tube waves to sense the increase in fluid communication between wellbore and formation caused by the opening of a hydraulic fracture.

No techniques are currently known for monitoring the completion environment comprised of both man-made (screen, casing, gravel sand) and natural (formation) components, permeability of which needs to be monitored over time. In the discussion below, we focus on laboratory experiment simulating realistic completions and comparing the results with analytical and numerical modeling.

Laboratory Setup with a Horizontal Well Model

Figure 3:
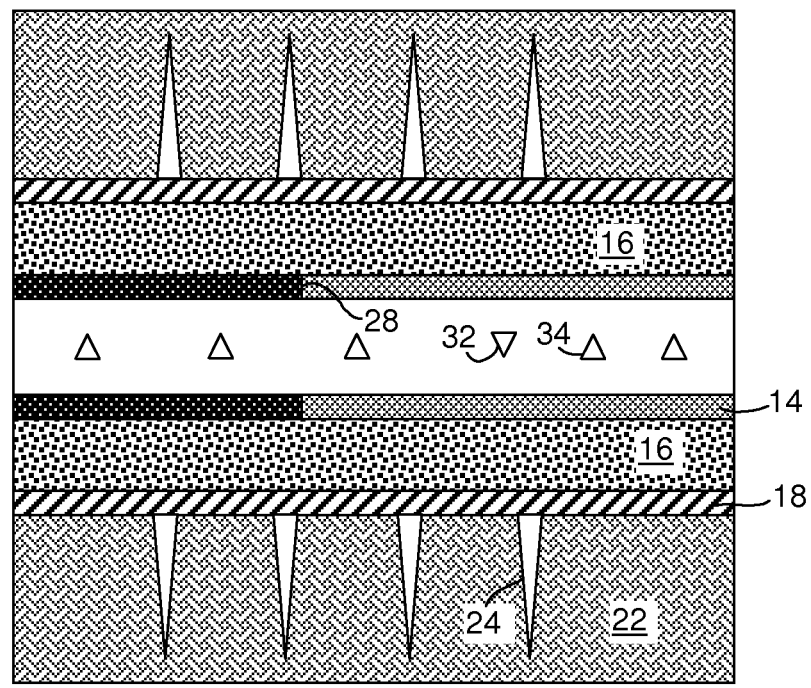
FIG. 3 schematically illustrates an experimental flow loop setup for modeling sand-screen completion in a horizontal well.

FIG. 3 depicts the schematics of a horizontal flowloop setup used for experimental measurements. In an experimental setup, the outer pipe (casing 18) of ~30 ft (9 m) length consisted of six 5-ft sections joined together and attached to the underlying support rail. The inner pipe (sand screen 14) was positioned inside using plastic centralizers. A source 32 and a plurality of sensors 34 were positioned inside the inner pipe.

It will be understood that the concepts of the present invention are applicable to systems in which the sensors are deployed on a wireline or are permanently placed in the hole. By way of example only, sensors could be embedded in the completion itself, mounted on any of the downhole tubulars, or included in the form of distributed sensors (which may be fiber optic sensors) that are wrapped around one or more of the downhole tubulars or devices.

Likewise, source 32 may comprise any suitable source, or a plurality of sources, and may be lowered into the hole or permanently deployed in the hole. Further, as discussed below, the source may be an effective source, and may be outside of the hole, so long as it is acoustically coupled to the fluid in the region of interest.

The annulus between the inner and the outer pipe can be filled either with water or water-saturated gravel sand. Measurements were conducted with a hydrophone array and a piezoelectric source lying at the bottom of the inner pipe. The source excited a broadband impulsive waveform with controlled dominant frequency. Twenty-four hydrophone sensors with 35 cm spacing recorded the resulting wavefield. To reduce background (building/air conditioning) noise stacking of multiple records was used.

We attempted to distinguish between four completion scenarios (Table 1) using tube-wave signatures. "Open" and "closed" denote two extreme cases of presence or absence of full fluid communication. "Partial" fluid communication should manifest itself with intermediate signatures between these two bounds. Signatures examined include propagation velocity and attenuation of tube waves as well as transmission and reflection amplitudes from interfaces such as at 28, where contacting media are described by different scenarios.

TABLE 1

Completion scenarios

|  | Screen | Perforations |
|---|---|---|
| Scenario 1 | Open | Closed |
| Scenario 2 | Closed | Closed |
| Scenario 3 | Open | Open |
| Scenario 4 | Closed | Open |

In the present disclosure we present experimental measurements for scenarios 1 and 2 in the absence of gravel sand and compare them with modeling. In the last section we present numerical modeling of gravel-packed completions for the first two scenarios.

Wave Propagation in a Simplified Completion Model as in Laboratory Setup (No Gravel Pack)

Here we present a simple model describing wave propagation in the laboratory setup. This model needs only minor modification to be applicable to the real in-situ environment. Actual sand screens can be quite complicated, but we start with the assumption that screen is represented by a homogeneous effective pipe both in terms of mechanical and hydraulic properties. If this pipe is not permeable (i.e., there is a plugged screen), then the laboratory setup can be simplified to this four-layered model: 1) fluid; 2) elastic inner pipe (screen); 3) fluid; 4) elastic outer pipe (casing). This model of two concentric elastic pipes with a free outer boundary (air) supports four axisymmetric wave modes at low frequencies:

TI—tube wave supported by the inner pipe
TO—tube wave supported by the outer pipe
PI—plate- or casing-type wave related to the inner pipe
PO—plate-type wave related to the outer pipe The Appendix to U.S. Application Ser. No. 61/004,877, which is incorporated herein by reference, describes the general nature of these modes and explains how the velocity of these modes can depend upon completion parameters. It will be understood, however, that the modes and the processing of the resultant signals can be performed using any of a number of mathematical techniques that are known to those skilled in the art.

Using the techniques described in the Appendix, we performed empirical analysis and modeling to determine the efficacy of the concepts claimed herein. Exemplary pressure seismograms for a four-layered model with closed pores (no gravel pack) from monopole source with successive amplifications, with the source central frequency equal to 1000 Hz showed that (a) the largest arrival is a fast tube wave (TO—1030 m/s) related to the stiff outer pipe, (b) the smaller arrival is a slow tube wave (TI—270 m/s) related to the softer inner pipe, and (c) plate waves are of even smaller amplitude (PO—

5410 m/s, PI—1630 m/s). The fast tube wave was least attenuated in the absence of a screen, somewhat attenuated in closed pores and substantially absorbed in open pores. Synthetic seismograms for an exemplary four-layered model were computed using a finite-difference code. In these models, the dominant arrival was found to be a fast tube wave associated with the outer pipe (TO), whereas the slow tube wave supported by the inner pipe (TI) was weaker and plate waves could only be seen with substantial amplification. Plate-wave velocities were found to be almost independent of frequency; the fast tube waves are slightly dispersive, whereas slow tube waves experience moderate dispersion. If formation is added outside the casing, then the outer plate wave (PO) disappears. If the annulus between the casing and the screen is filled with sand, then there is only one tube wave and one plate wave associated with the composite structure of the completion. Thus, the presence of two tube waves can be used as a diagnostic for a completion without a gravel pack (or fluidized gravel pack). Properties of tube waves in a gravel-packed completion are examined below.

If the inner pipe becomes permeable (as in a sand screen that is open to flow), then the same number of wavemodes remain, but their velocities and attenuation are altered. Simply speaking, both tube waves experience attenuation and a reduction in velocity.

In our modeling, sand screens open to flow were modeled as a homogeneous pipe made of effective poroelastic Biot material. Resorting to effective medium theory may not be fully justified since microelements such as perforations in a base pipe or slots are of the same dimensions as the pipe thickness. Nevertheless, data suggest that tube waves with wavelength of several meters "see" the screen as an effective pipe and justify a the use of simple model for understanding the effect of permeability changes on tube-wave signatures. Thus, the radial permeability of the experimental screens was estimated using a simple analytical model with an array of parallel slits or fractures.

In cases when perforations are closed (scenario 1 and 2), the outer boundary is considered as an impermeable pipe with a traction-free outer boundary. Complete plugging (scenario 2) was modeled as a no-flow boundary condition between the screen and the surrounding fluids.

Completion without Gravel Pack: Experiment Vs. Modeling

Experiments were conducted with a glass outer pipe and a PVC inner pipe. To model an open sand screen ("open pores") we used a PVC pipe with 0.0002 m (0.008") slots. Plugged sand screen was modeled with a blank PVC pipe without slots and is sometimes also referred to as "closed pores."

A. Transmission Signatures.

Turning first to transmission signatures—velocity and attenuation—in the presence of open and plugged screens, we compared wave-fields recorded in the case of no screen and screen with "open" and "closed" pores. In the absence of a screen, we found that there is only one (fast) tube wave present with velocity of about 1050 m/s. It experiences some amplitude loss, possibly due to intrinsic attenuation in the glass as well as in the thick recording cable. When an impermeable inner pipe is added (closed pores), an additional slow tube wave appears, whereas the fast wave starts to be slightly more attenuated due to high absorption in the PVC. With a slotted inner pipe, fluid communicates across the PVC screen, which causes a relatively strong attenuation of both tube waves. As used herein, the term "relatively strong attenuation" refers to attenuation that is greater than the attenuation experienced by the fast wave traveling through a medium that is known to be relatively impermeable, as compared to the completion or region of interest. Median filtering can separate fast wave and slow wave and reveal the presence of multiple reflections of each wave at the joints between the 5-ft pipe segments. We found that the slow wave was absent without a screen, present in a screen with closed pores and more attenuated and slower in open pores. Thus, we conclude that greatly increased attenuation of both fast and slow tube waves is the first-order diagnostic for open screens ("open pores"), whereas reduced attenuation is characteristic for plugged screens ("closed pores").

When it is determined that all or a portion of a completion is plugged, it may be desirable to adjust the properties of fluids in the borehole so as to reduce or eliminate the plugging. This may be accomplished, by, for example, adjusting the drawdown pressure, pulsing the pressure, modifying the fluid composition, or other techniques such as are known in the art.

Additional diagnostics can be established by analyzing energy distribution as a function of frequency between these two cases. Since the experimental data are complicated by the presence of additional reflections at the pipe joints, this analysis is preferably performed using slowness-frequency spectra. Slowness-frequency spectrum for the synthetic seismograms show that the fast tube wave dominates the spectrum. For closed pore the slow tube wave was well seen, with a broadening peak towards lower frequencies indicating dispersion. In the presence of open slots, the fast wave experiences strong attenuation that is particularly anomalous in the medium frequency range (350-700 Hz).

In a plot of the averaged velocity spectrum over the entire frequency range, both fast and slow tube waves with approximately the same velocities of 350 m/s and 1100 m/s were present in the plugged and open cases but the slow wave was completely absent without a screen. In a plugged screen the fast wave carried a maximum energy in the frequency range of 300-600 Hz, close to the dominant frequency of the source, whereas lower and higher frequencies carried less energy.

In contrast, the spectrum of the fast wave in an open screen had a big energy "hole" between 300 and 600 Hz where fast the wave was attenuated so strongly that even higher frequencies (600-900 Hz) carried more energy. As for the slow tube wave, it mainly existed at frequencies below 600 Hz and was also attenuated. Surprisingly its amplitude increased at low frequencies for open pores, where it was larger than the amplitude of the fast wave.

This experimental behavior was then compared with results predicted using numerical modeling. A plot of theoretical dispersion curves for the case of closed pores reveals that the fast tube wave experiences little dispersion below 2000 Hz and matches experimentally observed values. Synthetic pressure seismograms computed for closed and open pores in an experimental setup using a reflectivity method show that in open pores slow tube waves transforms to a rather complicated packet of energy with rather low velocities and a "stairstep" pattern. Lines drawn connecting the break in the phase have slopes close to slow P-wave velocity in the porous screen material. Increasing the diameter of the impermeable inner pipe is expected to result in a slowdown of the second tube wave velocity from 350 to 280 m/s. While for closed pores the slow velocity is well matched, for open pores the velocity is higher than predicted. Most likely this is the result of variation in elastic properties of the PVC used for manufacturing the blank pipe and the slotted screen. Synthetic seismograms were computed for a glass setup with our best estimate of poroelastic parameters of our experimental setup. As in the case of the experimental results, in the case of closed pores we observed two tube waves, with the fast tube wave dominating in amplitude. In the presence of a screen with open slots, both waves experienced strong changes. The fast tube wave experienced moderate attenuation and change of waveform. The slow tube wave was transformed into a complex packet with weak amplitude, rather slow velocities and a very strange character. By connecting the points where the phase changes inside the packet, we derived an approximation of the velocity of propagating slow Biot's wave in the porous screen material (~80 m/s). Since central frequency of the source (500 Hz) was much higher than critical Biot frequency (30 hz), the interference with slow Biot wave in the porous screen may be a reason for a complicated wave packet.

Without limiting the scope of the invention in any way, the following physical interpretation is suggested for the modeled results. A tube wave is born when the piston-like motion of the fluid inside the pipe creates a radial expansion that is resisted by the elastic pipe. The slow wave is mainly supported by the inner pipe. When this pipe is slotted, radial movement of the fluid is no longer resisted, as liquid can freely escape to the annulus, thus leading to a strong attenuation of this wave. In contrast, the fast wave is mainly supported by the outer glass solid pipe. When the inner pipe is permeable, piston-like motion of the fluid in the fast wave can additionally exchange the fluid between the outer and the inner fluid columns, thus creating a moderate attenuation.

Plots of slowness-frequency spectra for open pores show that, similar to the experimental results, the fast wave experiences anomalously high attenuation in the medium frequency range of 350-700 Hz. In addition, velocity is reduced at low frequencies and the energy peak becomes broader, indicating dispersion. Plots of energy distribution (left) and peak velocity (right) for the fast tube wave in the synthetic data confirm that the fast tube wave in an open screen is slowed at low frequencies but experiences slight acceleration at high frequencies. Comparison of the plots confirms the qualitative agreement between experiment and modeling: in both cases the fast wave exhibits anomalous amplitude decrease in the medium frequency range, while preserving its higher and lower frequencies. This amplitude decrease cannot be explained by the spectra of the source wavelet and therefore should be attributed to anomalous attenuation caused by fluid movement through the slotted porous screen.

The frequency range exhibiting resonance attenuation is controlled by permeability. For instance, when permeability decreases to 50 D, this band moves from 350-700 Hz to 600-1000 Hz, i.e. the lower the permeability, the higher the frequency of the band with anomalous attenuation of the fast wave. This is also consistent with experimental data, since plugged screens (0 Darcy) do not exhibit anomalous attenuation because the attenuated band will be at very high or infinite frequencies. Therefore the central frequency of the band with anomalous attenuation of the fast tube wave can be used as an additional robust diagnostic of the screen permeability. We should note that in both cases central frequency of the source is preferably much higher than the critical Biot frequency for the screen. It remains unexplained why in open pores modeling predicts rather strong dissipation, unusual characteristics and strong slowdown of the slow tube wave, whereas experiments show that the slow wave is simpler and of comparable amplitude to the fast wave at low frequencies.

The difference in velocity and attenuation between completions with open and plugged screens also leads to reflections at the boundaries where properties change. The following paragraphs discuss transmission-reflection at a single interface between open and plugged sections of the screen.

Interface Plugged-Open.

First, we used an experimental model in which ⅔ of the pipe length comprise a blank pipe (closed pores), and the remaining ⅓ comprised a slotted screen. At low frequencies, a source located in the middle of the blank pipe excites both fast and slow waves. The fast wave is highly attenuated upon reaching the interface, eg. at 28 in FIG. 3. The slow wave experiences strong reflection that is more easily seen on the wavefield-separated display. At higher frequencies, fast-wave reflections become more observable. Modeling shows qualitatively similar behavior. First, the fast wave becomes more attenuated in the open section. Second, while we observe both fast-fast and slow-slow reflections, the latter is substantially larger in amplitude, which is consistent with the experimental data. As above, it is observed that modeling underestimates the amplitude of the slow wave in open pores.

Interface Open-Plugged

When the source is inside the open section then wave propagation changes. First, at low frequencies the slow tube wave (~300 m/s) dominating wave propagation in the open section converts effectively into a fast wave (~1000 m/s) in the plugged section. The interference between the strongly attenuating fast and slow waves creates the impression of a curved moveout around the source, however it is clear that the fast wave is born by a late-arriving direct slow wave. A simple inspection of unprocessed gather reveals the location of the open-plugged interface as the change in the slope of the dominant events. Second, the same incident slow wave generates a strong reflection back into the open section that is clearly larger than the earlier reflection from a pipe joint. Third, at higher frequencies we observed a direct fast wave from the source that quickly attenuated in the open section but converted to a fast wave that experiences less attenuation in the closed section. Nevertheless, a stronger right-going fast wave is born by conversion from a later slow tube wave.

Completion with a Gravel Pack—Numerical Modeling

In order to understand the influence of gravel sand on wave propagation it is important to properly predict the shear modulus of the sand. There are two possible scenarios:

If the shear modulus is small but non-vanishing, the gravel pack is similar to a layer of a weak elastic material. In this case, the completion behaves as a composite (radially layered) poroelastic surrounding consisting of a sand screen, gravel sand, and casing—all with a non-zero shear rigidity. If all layers are fully bonded, only a single tube wave exists.

If the shear modulus of sand is zero, the gravel acts as a suspension and its behavior is similar to an effective high-density fluid but complicated by finite porosity and permeability. More than one tube wave would be observed in this case, making it similar to the case of a completion without a gravel pack.

Based on our studies, it is believed that in the normal case of good-quality gravel packs the first scenario takes place. This is confirmed by visual inspection of gravel packing procedures at the lab: once sand particles are packed, they do not move with the flow and remain "locked" in place. That is indicative of grain-to-grain contact and non-vanishing shear rigidity. The second scenario may occur in case of fluidized sand when flow destabilizes the gravel pack and grain-to-grain contact no longer takes place. In the following discussion, we concentrate on the "normal" first scenario when the gravel pack is modeled as a layer of poroelastic Biot medium. Shear-wave velocity remains the most uncertain parameter. For initial modeling we have taken a value of 70 m/s that lies between in-situ estimates of ~120-150 m/s and laboratory estimates of ~10-20 m/s.

In the next section we analyze wave propagation in the model describing the laboratory aluminum setup that would be used for an actual experiment with a gravel pack in the future. Thus we examine four-layer model with a free outer boundary consisting of: 1) fluid; 2) elastic inner pipe (screen); 3) sand; and 4) elastic outer pipe (casing).

Transmission Signatures

If the poroelastic nature of sand and screen are neglected and are modeled as elastic impermeable media, then only two axisymmetric modes propagate at low frequencies:

T—tube wave supported by the composite pipe consisting of screen, sand and casing;

P—plate- or casing-type wave supported by the composite pipe.

Thus a gravel-packed completion has half as many modes as a completion without gravel pack. This greatly simplifies wave propagation. A composite tube wave is closer in character to fast tube wave and even maintains a similar velocity of ~1100 m/s. When the sand becomes fluidized then a second (slow) tube wave emerges that is similar to the case of a completion without a gravel pack. Therefore the presence of second slow tube wave is a diagnostic of completions with fluidized sand or lack of sand. The plate wave has a drastically lower velocity and becomes strongly dispersive due to highly contrasting elastic properties of the completion layers.

Finally, it should be noted that additional axisymmetric modes appear at higher frequencies. Cut-off frequencies of the higher-order mode decrease with decreasing shear velocity of the sand. As a result, a very low shear velocity of the sand may create a complex multi-mode wave propagation.

Synthetic seismograms show that the tube-wave dominates wave propagation at low frequencies, while the plate wave can only be seen with high amplification. In the plugged section of the screen (closed pores) the tube wave has a higher velocity and experiences very little attenuation, as expected. In contrast, open pores allow fluid communication between the liquid column inside the screen and pore fluid in the sand. As a result, we observe a strong dispersion and a reduction in velocity as well as substantial attenuation even at very short offsets. Thus, similar to open-hole logging methods, we can distinguish permeable and impermeable sections of the screen by examining velocity and attenuation. Slow-down in velocity and high attenuation are simple diagnostics of an open section, whereas speed-up and little or no attenuation are characteristics of a plugged section.

Reflection Signatures

The synthetic seismograms also illustrate the reflection-transmission process at the plugged-open and open-plugged interface. Wave propagation is simplified compared to the case of no gravel pack, since only a single tube wave is present in the open and plugged sections. The reflected tube wave is due to the difference in velocities and attenuations across the interface. Interestingly, in the model, the reflected wave from the closed-open interface is very large (about 35%), whereas the reflected wave from the open-plugged interface is weaker (about 5%). It is tempting to use 1D effective wavenumber approach to gain an insight into the physics of the reflection-transmission process. While this approach has been validated for poroelastic media and radially inhomogeneous elastic media, its validity for radially layered poroelastic media is yet to be established. Nonetheless, using a the 1D assumption, the effective wavenumber approach predicts that the reflection coefficients at plugged-open and open-plugged interfaces should be of the same magnitude and opposite sign, which contradicts the finite-difference modeling.

Fiber-Optic Devices

As discussed above, laboratory experiments and modeling prove the concept of using tube-wave signals to monitoring permeability changes along the completion. However, in order to implement this technique downhole, it is necessary to provide acoustic sources and receivers in a producing well. Tools used in the lab are not applicable for downhole deployment; downhole deployment requires that the sources and receivers be protected and not obstruct the flow.

Sensors

With respect to receivers, these objectives can be met by fiber-optic sensors placed on the outside of the pipe (sand screen, tubing or casing). In addition, such sensors can be completely passive and therefore do not require electric power. We tested this idea by comparing hydrophone recording inside the plastic pipe with fiber-optic "on the pipe" seismograms. Good agreement was observed between the two sets of measurements.

While inside the pipe at low frequencies both tube and plate waves are described by piston-like motion, on the pipe wall tube waves produce mainly radial displacement, while plate waves produce mainly axial displacement. A fiber wrapped around the pipe detects the radial displacement of the pipe, which is characteristic of tube waves—sometimes called "breathing" modes. In addition, azimuthal averaging performed by fiber-optic sensors tends to suppress other noises and highlight the axisymmetric tube wave.

Wrapping fiber on the outside of the sand screen or casing can be implemented using a real-time casing imaging (RTCI) tool that aims at measuring deformations of the pipe. RTCI sensors tend to be closely spaced to detect asymmetric quasi-static deformations, whereas the present real-time completion monitoring (RTCM) preferably uses an average around the circumference of the pipe at discrete locations but at fine sampling interval in time.

Laboratory Fiber-Optic System

The current fiber optic system used in the test setup was an interferometric system based on Michelson interferometers. A Michelson interferometer consists of a signal splitter, a reference coil, a sensing coil and two Faraday Rotating Mirrors (FRMs), one placed at the end of each fiber coil. The modulated light from the laser is split and travels down the reference and sensing coils. Both signals reflect at the FRMs and travel back to the splitter, where they interfere and the light is routed back to the opto-electronics using the second fiber lead.

The sensing coil is wrapped around the pipe and experiences strain as the pipe breathes. The reference coil is preferably located very close to the sensing coil, so as to minimize any noise pick-up before the signals interfere. The point of interference between the sensing signal and reference coil is the splitter/combiner, which is co-located downhole with the coils. The strain induced in the pipe during the breathing motion causes a dynamic change in optical path length in the sensing coil compared with the reference coil. The change in optical path length causes a shift in the interferometric signal, which in turn can be related to the magnitude and frequency of the breathing motion of the pipe.

The main benefit of this scheme is the ease of installation and flexibility to move individual sensors between different locations on the pipe as well as between different test setups. An experimental system with 24 sensors uses 48 fiber optic leads, which is manageable in a laboratory environment but impractical for a field deployment.

Fiber-Optic System for Field Installation

A system for field deployment would preferably use a signal multiplexing scheme based on Frequency Division Multiplexing (FDM) and Wavelength Division Multiplexing (WDM), which would reduce the number of fiber optic leads running from the sensing section to the surface. The reference coil of the Michelson interferometer is not preferred for field deployment, as the reference coil would require some space between the tubing and casing. The selected Michelson interferometric system is ideal for the current laboratory experiments where a high degree of flexibility is desired, combined with the highest possible performance and noise cancellation. It may however be sub-optimal from an overall deployment perspective, given its mechanical footprint.

Other techniques for making the desired measurements exist and may also be practical for field deployment. Two options in particular offer good performance and may be compatible with the present system. Both of these systems use a continuous optical fiber.

The first technology is based on the Fabry-Perot interferometer, where reflective mirrors are engraved in the optical fiber. The engraved sensing coil is wrapped around the pipe, as for the Michelson interferometer, and experiences strain as the pipe breathes. The reference coil is relatively far from the sensing coil and the signal pulses may pick-up noise as they travel up the cable before the signals interfere. The strain induced in the pipe during the breathing motion causes a dynamic change in optical path length in the sensing coil compared with the reference coil. The change in optical path length causes a shift in the interferometric signal, which in turn can be related to the magnitude and frequency of the breathing motion of the pipe. The benefit of the Fabry-Perot system is the smaller down-hole footprint. The drawback is the potentially higher noise that maybe picked up by the cable connecting the sensors to the surface opto-electronics.

The second technology, "Blue ROSE", was developed by the Naval Undersea Warfare Center for military security application, in which 'ROSE' is an acronym for Rayleigh Optical Scattering and Encoding. The Blue ROSE technology detects Rayleigh backscattering profiles (or "fingerprints") along the length of the fiber. Each segment of the optical fiber has a unique scattering profile due to the random impurities in the fiber that causes Rayleigh scattering. The Blue ROSE system uses the Rayleigh fingerprints in the optical fiber as a Fabry-Perot reflectors. The system can dynamically use different Rayleigh fingerprints anywhere along the length of the fiber. Blue ROSE has the potential to combine both the RTCI and RTCM systems in a single cable, which would be desirable for complete downhole surveillance.

Sources

Both transmission and reflection configuration of RTCM require repeatable excitation of the tube wave downhole. This can be achieved in the two different ways described below, using both active sources and passive sources.

Active Sources

In principle, a dedicated active source can be mechanically clamped on the outside of the tubing or screen similar to and can be mechanical or magnetostrictive. Apart from additional installation in the well, this approach also requires electric power cable to supply the source.

Passive Noise Sources

A less demanding alternative may be to use flow noise or other disturbances as a passive signal and obtain response between two sensors using cross-correlation. So called "noise correlators" have been used to detect the location of subsurface leaks in the pipes. Lately, similar cross-correlation technique of fiber-optic on-the pipe sensors was utilized to measure tube-wave velocity and invert for fluid composition and flow speed in surface and downhole pipes. In the downhole case, the acoustic flowmeter preferably comprises an array of fiber-optic sensors installed on the outside of the tubing near the completion and performs acoustic measurements in real time while the well is flowing.

Effective Source

Cross-correlation is a 1D version of the more general Virtual Source™ method described in U.S. Pat. No. 6,747,915 and international application WO2008064100. After cross-correlation of, for example, a recording at the first receiver with those at the remaining sensors it is possible to obtain a response as if the signal had been actually emitted from a "effective source" placed at the location of the first receiver. Since we directly measure the incident signal in the effective source—we know the source signature and can shape it to as desired. This is important, as it can allow two important steps—the stacking of multiple records shaped with the same source signature to improve signal-to-noise ratio, and evaluation of not only velocity but also attenuation of the tube-wave signals. Thus, in some embodiments, the virtual source method is used to allow the implementation of a completely passive version of RTCM without active sources downhole.

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the scope of the invention.

Discussion of Experimental Setup

The initial flow-loop setup with Plexiglas pipe and PVC screens was not well suited for acoustic measurements because of extremely high attenuation and slow velocities. It was also not representative in terms of acoustical properties to a field case with steel tubulars. The glass setup used in the current experiments was an improvement, but still remained suboptimal due to acoustically slow and attenuative PVC screens as well as due to strong inter-joint reflections that contaminated the data. While processing partly helped to deal with these parasitic reflections, joints of such design are not representative of a field case and thus should be avoided. It is preferable to use an aluminum setup with aluminum outer pipe and aluminum screens to reach fast acoustic velocities typical for steel tubulars while still remain at a low weight that can be handled in the lab. To avoid inter-joint reflections, it is advisable to reduce number of pipe sections and suspend the pipe off the slings.

Acoustic Acquisition

Acoustic acquisition in the lab utilized 24 sensors at 35 cm spacing. To avoid aliasing, it is preferred to have a sensor spacing equal or smaller than ½ wavelength of wave of interest computed at the dominant frequency. Thus for gravel-packed completions with expected velocities of ~700 m/s and central frequency ~700 Hz, the wavelength is ~1 m and spacing of 0.5 m or less is preferred. In completions with no gravel pack, or if fluidization is suspected, slow tube-wave velocities of ~300 m/s are expected and smaller sampling intervals are desirable. Of course, if a lower frequency can be used in a satisfactory manner—then sampling can be increased, however lower frequency tends to produce lower spatial resolution.

We have also discovered that slow tube wave modes can be excited in open annular regions, and these waves can be detected. Thus, in-well and in-annulus conditions can be determined using tube wave recordings from active and/or passive sources. This technique is useful for, for example, identifying un-cemented or partially-cemented annular regions behind casing in a well. This method would complement more conventional logging techniques. Moreover, passive observations of these tube wave modes could be indicative of phenomena such as behind-casing flow or casing deformation acting as sources. Some embodiments of the invention therefore include transmitting an acoustic signal to fluid that may be acoustically coupled to the annulus and inferring that the layer of cement is incomplete if a slow annular tube wave mode is observed.

REFERENCE TO APPENDIX

An appendix comprising zero-frequency velocity in models with one and two concentric pipes was attached to the parent application from which this application claims priority, the entire contents of which are incorporated herein by reference.

Other and further embodiments utilizing one or more aspects of the inventions described above can be devised without departing from the scope of the invention. For example, the real-time acoustic monitoring techniques described herein can be applied to not only the monitoring of sand-screened and gravel packed completions, but also to other completion and downhole applications, such as recovery operations. Further, the various methods and embodiments of the real-time acoustic monitoring methods can be included in combination with each other to produce variations of the disclosed methods, apparatus, and embodiments.

The order of steps can occur in a variety of sequences unless otherwise specifically limited. The various steps described herein can be combined with other steps, interlineated with the stated steps, and/or split into multiple steps. Similarly, elements that have been described functionally can be embodied as separate components or can be combined into components having multiple functions.

The inventions have been described in the context of preferred and other embodiments and not every embodiment of the invention has been described. Obvious modifications and alterations to the described embodiments are available to those of ordinary skill in the art. The disclosed and undisclosed embodiments are not intended to limit or restrict the scope or applicability of the invention conceived of by the Applicants, but rather, in conformity with the patent laws, Applicants intend to fully protect all such modifications and improvements that come within the scope or range of equivalent of the following claims.

What is claimed is:

1. A method for monitoring fluid flow through a permeable downhole device in a borehole, comprising:
    a) providing an acoustic tube wave in fluid in the device;
    b) measuring the acoustic tube wave after it has passed through the fluid in the device; and
    c) assessing the permeability of the device by measuring the attenuation of the acoustic signal and determining that the device is at least partially plugged by detecting at least one of a reduction in attenuation or a reduction in velocity loss in the tube wave as it passes through the device.

2. The method according to claim 1 wherein step c) further includes measuring changes in velocity of the acoustic signal.

3. The method according to claim 1, further including adjusting the properties of fluids in the borehole in response to a determination that the device is at least partially plugged.

4. The method according to claim 1 wherein the device is selected from the group consisting of sand screens, gravel packs, gravel pack screens, wire wrapped screens, mechanical screens, screens having a fully or partially perforated base pipe and a filter medium disposed thereon, and perforated casing.

5. The method according to claim 1 wherein the device is a gravel packing device and wherein the measurements made in step c) are indicative of properties of a gravel packing process.

6. The method according to claim 1 wherein the measurements in step b) are made using a plurality of sensors deployed in the borehole.

7. The method according to claim 6 wherein the sensors are permanently deployed in the borehole.

8. The method according to claim 6 wherein the sensors are fiber optic sensors.

9. The method according to claim 8 wherein the sensors are supported on a device that is wrapped around at least one of a sand screen and downhole tubular.

10. A method for producing hydrocarbons from a hydrocarbon-bearing formation, comprising producing hydrocarbons through a permeable downhole device and monitoring the flow through the device using the method of claim 1.

11. A method for monitoring fluid flow through a permeable downhole device in a borehole, comprising:
    a) providing an acoustic tube wave in fluid in the device;
    b) using a plurality of sensors deployed in the borehole to measure the acoustic tube wave after it has passed through the fluid in the device;
    c) assessing the permeability of the device by measuring the attenuation of the acoustic signal; and
    d) cross-correlating a signal received at a first receiver with signals received at additional sensors so as to obtain an effective response as if the signal had been emitted from a source at the position of said first receiver.

12. A method for monitoring fluid flow through a permeable downhole device in a borehole, comprising:
    a) providing an acoustic tube wave in fluid in the device;
    b) measuring the acoustic tube wave after it has passed through the fluid in the device; and
    c) assessing the permeability of the device by measuring the attenuation of the acoustic signal; wherein step c) further includes determining that the device is not plugged by detecting that a fast tube wave passing through the device is slowed at low frequencies but is accelerated at high frequencies.

13. A method for monitoring fluid flow through a permeable downhole device in a borehole, comprising:
    a) providing an acoustic tube wave in fluid in the device;
    b) measuring the acoustic tube wave after it has passed through the fluid in the device;
    c) assessing the permeability of the device by measuring the attenuation of the acoustic signal; and
    further including the step of determining the relative permeability of the device by detecting a frequency band having a relatively high degree of attenuation and comparing the frequency of said band to that of a frequency band having a relatively high degree of attenuation in a different measurement.

14. A method for monitoring fluid flow through a permeable downhole device in a borehole, comprising:
    a) providing an acoustic tube wave in fluid in the device;
    b) measuring the acoustic tube wave after it has passed through the fluid in the device; and
    c) assessing the permeability of the device by measuring the attenuation of the acoustic signal; wherein step c) further includes determining that the device is not plugged by measuring a fast wave and detecting a relatively strong attenuation of said fast wave.

15. A method for monitoring fluid flow through a permeable downhole device in a borehole, comprising:
- a) providing an acoustic tube wave in fluid in the device;
- b) measuring the acoustic tube wave after it has passed through the fluid in the device; and
- c) assessing the permeability of the device by measuring the attenuation of the acoustic signal; wherein step c) further includes determining that the device is not plugged by detecting a slow tube wave with reduced amplitude and velocity.

* * * * *